(12) United States Patent
Liu et al.

(10) Patent No.: US 10,048,178 B2
(45) Date of Patent: Aug. 14, 2018

(54) ROCK SPECIMEN AND METHOD FOR TESTING DIRECT TENSILE STRENGTH OF THE SAME

(71) Applicant: Sichuan University, Chengdu (CN)

(72) Inventors: Jianfeng Liu, Chengdu (CN); Heping Xie, Chengdu (CN); Lu Wang, Chengdu (CN); Jianliang Pei, Chengdu (CN); Yu Bian, Chengdu (CN); Huining Xu, Chengdu (CN); Yong Xiang, Chengdu (CN); Fei Wu, Chengdu (CN); Hang Zou, Chengdu (CN); Yangmengdi Xu, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 412 days.

(21) Appl. No.: 14/880,201

(22) Filed: Oct. 10, 2015

(65) Prior Publication Data
US 2016/0103047 A1   Apr. 14, 2016

(30) Foreign Application Priority Data
Oct. 11, 2014   (CN) .......................... 2014 1 0532301

(51) Int. Cl.
*G01N 3/20* (2006.01)
*G01N 3/08* (2006.01)

(52) U.S. Cl.
CPC ....... *G01N 3/08* (2013.01); *G01N 2203/0298* (2013.01)

(58) Field of Classification Search
CPC ............ G01N 3/08; G01N 3/24; G01N 33/24; G01N 2203/0298
See application file for complete search history.

(56) References Cited

U.S. PATENT DOCUMENTS

| 4,444,058 A | * | 4/1984 | Ratigan | .................... G01N 3/08 73/834 |
| 2013/0233536 A1 | * | 9/2013 | Alqam | ..................... G01N 3/00 166/250.01 |

FOREIGN PATENT DOCUMENTS

JP        2008275319        * 11/2008   ............... G01N 3/20

* cited by examiner

*Primary Examiner* — Blake A Tankersley
(74) *Attorney, Agent, or Firm* — Matthias Scholl, PC; Matthias Scholl

(57) ABSTRACT

A rock specimen, including a rock body having the shape of a cylinder or a regular square prism. The rock body includes: an upper end face, a first circular groove, a first cylinder, a first circular body, a lower end face, a second circular groove, a second cylinder, and a second circular body. The first circular groove is disposed on the upper end face of the rock body and has a circle center coinciding with the center of the upper end face of the rock body. The second circular groove is disposed on the lower end face of the rock body and has a circle center coinciding with the center of the lower end face of the rock body. The outer diameter of the first circular groove is smaller than the inner diameter of the second circular groove, and the first circular groove and the second circular groove are staggered.

10 Claims, 5 Drawing Sheets

ROCK SPECIMEN AND METHOD FOR TESTING DIRECT TENSILE STRENGTH OF THE SAME

CROSS-REFERENCE TO RELATED APPLICATIONS

Pursuant to 35 U.S.C. § 119 and the Paris Convention Treaty, this application claims the benefit of Chinese Patent Application No. 201410532301.9 filed Oct. 11, 2014, the contents of which are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a rock specimen and a method for testing direct tensile strength of the same.

Description of the Related Art

Methods of testing tensile strength of rocks include indirect testing methods and direct testing method. The indirect testing methods are inaccurate. The direct testing method requires bonding or clamping the testing samples, which is time-consuming and has a low success rate. In addition, the bonding or clamping position of the testing samples is easily damaged, and thus high standard and high specification of testing devices are required, which increases the operational costs.

SUMMARY OF THE INVENTION

In view of the above-described problems, it is one objective of the invention to provide a rock specimen and an improved method for testing direct tensile strength of the same. The method is adapted to measure the tensile strength of the rock specimen with high measurement accuracy and high test success rate.

To achieve the above objective, in accordance with one embodiment of the invention, there is provided a first rock specimen for direct tensile test. The rock specimen comprises a rock body having a shape of a cylinder or a regular square prism. The rock body comprises: an upper end face, a first circular groove, a first cylinder, a first circular body, a lower end face, a second circular groove, a second cylinder, and a second circular body. The upper end face is in parallel with the lower end face. The first circular groove is disposed on the upper end face of the rock body and has a circle center coinciding with a center of the upper end face of the rock body. The second circular groove is disposed on the lower end face of the rock body and has a circle center coinciding with the center of the lower end face of the rock body. An outer diameter of the first circular groove is smaller than an inner diameter of the second circular groove, and the first circular groove and the second circular groove are staggered. The first circular groove divides a first part of the rock body into the first cylinder located at the center and the first circular body surrounding the first cylinder. The second circular groove divides a second part of the rock body into the second cylinder located at the center and the second circular body surrounding the second cylinder. A diameter of the first cylinder is smaller than a diameter of the second cylinder. An end face of the first cylinder and an end face of the first circular body are disposed on a same plane. An end face of the second cylinder and an end face of the second circular body are disposed on a same plane.

In a class of this embodiment, the diameter of the first cylinder is between ¼ and ⅓ of a diameter of the rock body having the shape of the cylinder or a side length of the rock body having the shape of the regular square prism. The diameter of the second cylinder is between 1.5 and 2 folds of the diameter of the first cylinder.

In a class of this embodiment, a width of the first circular groove is between 2 and 10 mm. A width of the second circular groove is between 2 and 10 mm. A depth of the first circular groove is between ½ and ⅘ of a height of the rock body. A depth of the second circular groove is between ⅔ and ⅘ of a height of the rock body.

In a class of this embodiment, the width of the first circular groove is between 3 and 5 mm. The width of the second circular groove is between 3 and 5 mm. The depth of the first circular groove is between ⅔ and ¾ of the height of the rock body. The depth of the second circular groove is between ⅔ and ¾ of the height of the rock body.

In accordance with another embodiment of the invention, there is provided a second rock specimen for direct tensile testing. The rock specimen comprises a rock body having a shape of a cylinder or a regular square prism. The rock body comprises: an upper end face, a first circular groove, a first cylinder, a first circular body, a lower end face, a second circular groove, a second cylinder, and a second circular body. The upper end face is in parallel with the lower end face. The first circular groove is disposed on the upper end face of the rock body and has a circle center coinciding with a center of the upper end face of the rock body. The second circular groove is disposed on the lower end face of the rock body and has a circle center coinciding with the center of the lower end face of the rock body. An outer diameter of the first circular groove is smaller than an inner diameter of the second circular groove, and the first circular groove and the second circular groove are staggered. The first circular groove divides a first part of the rock body into the first cylinder located at the center and the first circular body surrounding the first cylinder. The second circular groove divides a second part of the rock body into the second cylinder located at the center and the second circular body surrounding the second cylinder. A diameter of the first cylinder is smaller than a diameter of the second cylinder. An end face of the first cylinder is higher than the end face of the first circular body, and an end face of the second circular body is lower than an end face of the second circular body.

In a class of this embodiment, a distance between the end face of the first cylinder and the end face of the first circular body is not larger than 10 mm.

In a class of this embodiment, the diameter of the first cylinder is between ¼ and ⅓ of a diameter of the rock body having the shape of the cylinder or a side length of the rock body having the shape of the regular square prism. The diameter of the second cylinder is between 1.5 and 2 folds of the diameter of the first cylinder. A width of the first circular groove is between 2 and 10 mm. A width of the second circular groove is between 2 and 10 mm. A depth of the first circular groove is between ½ and ⅘ of a height of the rock body. A depth of the second circular groove is between ⅔ and ⅘ of a height of the rock body.

In a class of this embodiment, the width of the first circular groove is between 3 and 5 mm. The width of the second circular groove is between 3 and 5 mm. The depth of the first circular groove is between ⅔ and ¾ of the height of the rock body. The depth of the second circular groove is between ⅔ and ¾ of the height of the rock body.

A method for manufacturing the rock specimen for direct tensile testing is as follows:

The rock collected from the field is processed by a rock cutting machine or/and a casing into a rock body having the shape of the cylinder or a rock body having the shape of the regular square prism, and polished by a polishing machine, so that the upper end face and the lower end face of the rock body having the shape of the cylinder or the rock body having the shape of the regular square prism meet the processing accuracy of end faces of the rock specimen for the rock compression test according to the standard test method of engineering rock. The upper end face of the rock body having the shape of the cylinder or the rock body having the shape of the regular square prism is subsequently processed by the casing to form the first circular groove adopting a center of the upper end face of the rock body as the circle center, and the lower end face of the rock body having the shape of the cylinder or the rock body having the shape of the regular square prism is processed to form the second circular groove adopting the center of the lower end face of the rock body as the circle center, so that the first rock specimen for the direct tensile test is manufactured. The rock cutting machine is utilized to cut part of the first circular body and part of the second cylinder from the first rock specimen for the direct tensile test to form the second rock specimen for the direct tensile test.

After the rock specimen is processed into the first rock specimen or the second rock specimen for the direct tensile test, a direct tensile test is conducted on the specimen.

In accordance with still another embodiment of the invention, there is provided a method for testing direct tensile strength of the rock specimen. The method comprises:

1) disposing a circular cushion block on a test bench of a rock mechanics testing system, in which an inner diameter of the circular cushion block is smaller than an inner diameter of the second circular body and is larger than the diameter of the second cylinder, and an outer diameter of the circular cushion block is larger than a diameter of the rock body having the shape of the cylinder or a side length of the rock body having the shape of the regular square prism;
2) disposing the rock specimen on the circular cushion block, allowing a center line of the rock specimen to coincide with a center line of the circular cushion block, and allowing the end face of the second circular body to contact an end face of the circular cushion block; and
3) disposing a cylindrical cushion block on the end face of the first cylinder of the rock specimen, in which a diameter of the cylindrical cushion block is larger than the diameter of the first cylinder and smaller than an inner diameter of the first circular body, and a center line of the cylindrical cushion block coincides with the center line of the rock specimen; and
4) operating the rock mechanics testing system, loading a pressure on the rock specimen via the cylindrical cushion block and the circular cushion block to stretch the rock specimen.

In accordance with still another embodiment of the invention, there is provided a method for direct shear testing of the rock specimen. The method comprises:

1) disposing the rock specimen on a test bench of a rock mechanics testing system, allowing the end face of the second circular body to contact the test bench; and
2) operating the rock mechanics testing system, loading a pressure on the rock specimen via the end face of the first cylinder and the end face of the second circular body to stretch the rock specimen.

Advantages of the rock specimens according to embodiments of the invention are summarized as follows:

1. The rock specimens for direct tensile testing are a new type of rock specimen, thereby enriching the existing types of the rock specimen for the direct tensile testing.
2. The rock specimen for the direct tensile test of the invention can be stretched by exerting pressures on the end face of the first cylinder and the end face of the second circular body. Thus, the difficulty to keep the tensile stress and the axial rock specimen in parallel in the bonding method is overcome, thereby ensuring the accuracy of the test result, and the test failure resulting from the stretch of the bonding position or the clamping position in the bonding method or the clamping method is also overcome. Thus, for the rock specimen, the test is available, and the success rate of the test is close to 100%.
3. The direct tensile test of the rock can be conducted in the common rock mechanics testing system.
4. The rock specimen for the direct tensile test of the invention has simple structure and is convenient for manufacture.

BRIEF DESCRIPTION OF THE DRAWINGS

The invention is described hereinbelow with reference to the accompanying drawings, in which.

Figure 1:
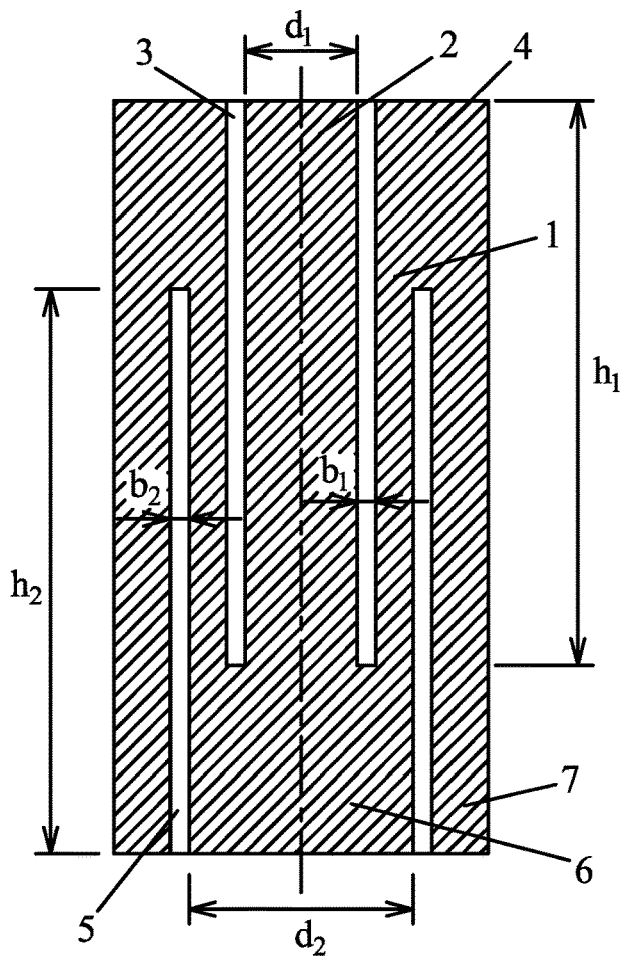
FIG. 1 is a sectional view of a first rock specimen for direct tensile testing in accordance with one embodiment of the invention.

In the drawings, the following reference numbers are used: 1. Rock body; 2. First cylinder; 3. First circular groove; 4. First circular body; 5. Second circular groove; 6. Second cylinder; 7. Second circular body; $d_1$. Diameter of a first cylinder; $d_2$. Diameter of second cylinder; $h_1$. Depth of first circular groove; $h_2$. Depth of second circular groove; $h_3$. Distance between end face of first cylinder and end face of first circular body; $b_1$. Width of first circular groove; $b_2$. Width of second circular groove; D. Diameter of rock body having the shape of the cylinder; and L. Side length of rock body having the shape of the regular square prism.

DETAILED DESCRIPTION OF THE EMBODIMENTS

For further illustrating the invention, experiments detailing a rock specimen and a method for testing direct tensile strength are described below. It should be noted that the following examples are intended to describe and not to limit the invention.

In the following examples, MTS Model 815 rock mechanics testing system was utilized to conduct the direct tensile test, and loading rates are 0.001 mm/s, 0.01 mm/s, 0.1 mm/s, 1 mm/s, 5 mm/s, and 7 mm/s.

Example 1

Figure 2:
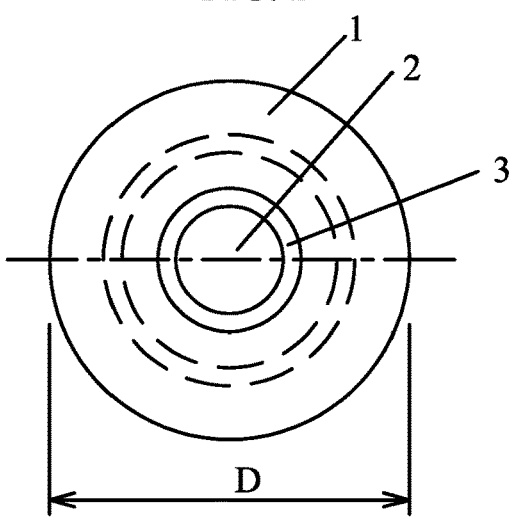
FIG. 2 is a top view of a rock body having the shape of the cylinder of FIG. 1.
Figure 3:
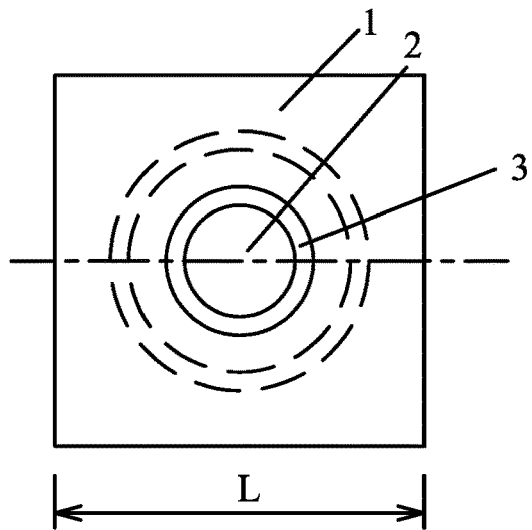
FIG. 3 is a top view of a rock body having the shape of the regular square prism of FIG. 1.

A rock specimen for direct tensile test, as shown in FIGS. 1-2, a rock body 1 of the rock specimen has the shape of a cylinder. An upper end face and a lower end face of the rock body are in parallel with each other. A first circular groove 3 is disposed on the upper end face of the rock body 1 and has a circle center coinciding with a center of the upper end face of the rock body 1. A second circular groove 5 is disposed on the lower end face of the rock body 1 and has a circle center coinciding with the center of the lower end face of the rock body 1. An outer diameter of the first circular groove 3 is smaller than an inner diameter of the second circular groove 5, and the first circular groove 3 and the second circular groove 5 are staggered. The first circular groove 3 divides an upper part of the rock body 1 into a first cylinder 2 located at the center and a first circular body 4 surrounding the first cylinder 2. The second circular groove 5 divides a lower part of the rock body 1 into a second cylinder 6 located at the center and a second circular body 7 surrounding the second cylinder 6. A diameter $d_1$ of the first cylinder 2 is smaller than a diameter $d_2$ of the second cylinder 6. An end face of the first cylinder 2 and an end face of the first circular body 4 are disposed on a same plane. An end face of the second cylinder 2 and an end face of the second circular body 7 are disposed on a same plane. Dimensions of different components of the rock specimen are as follows:

The rock body has a diameter D of 100 mm and a height of 60 mm. A width $b_1$ of the first circular groove 3 and a width $b_2$ of the second circular groove 5 are the same and equal to 2 mm. The first circular groove 3 has a height $h_1$ of 30 mm, and the second circular groove 5 has a height $h_2$ of 40 mm. The first cylinder 2 has the diameter $d_1$ of 25 mm, and the second cylinder 6 has a diameter $d_2$ of 50 mm. The diameter of the first cylinder 2 is an inner diameter of the first circular groove 3, and the diameter of the second cylinder 6 is an inner diameter of the second circular groove 7.

The direct tensile test of the rock specimen is conducted as follows:

1) A circular cushion block 9 is disposed on a test bench of a rock mechanics testing system, in which, an inner diameter of the circular cushion block is 52 mm, and an outer diameter of the circular cushion block is 105 mm.

Figure 7:
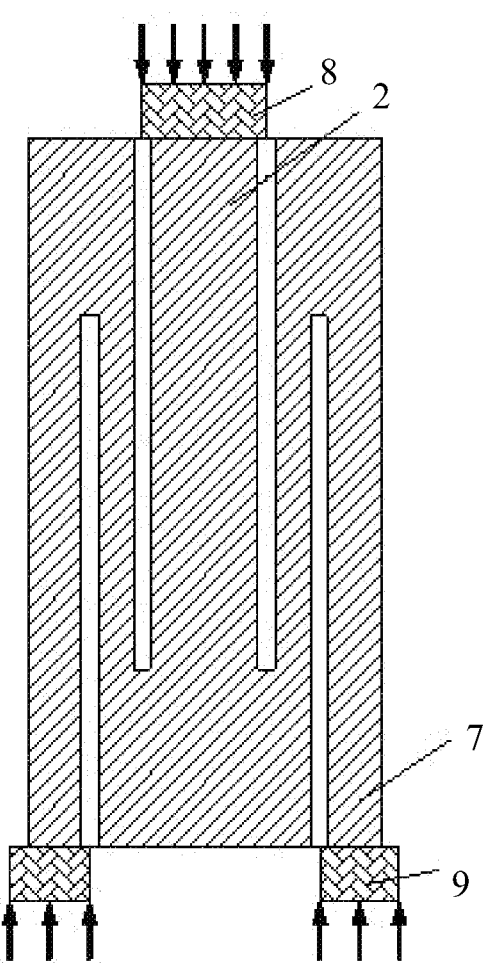
FIG. 7 is a sectional view showing a rock specimen of FIG. 1 mounted on a test bench of a rock mechanics testing system and pressures loaded on the rock specimen.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 27 mm, and a center line of the cylindrical cushion block 8 coincides with the center line of the rock specimen (as shown in FIG. 7).

Figure 9:
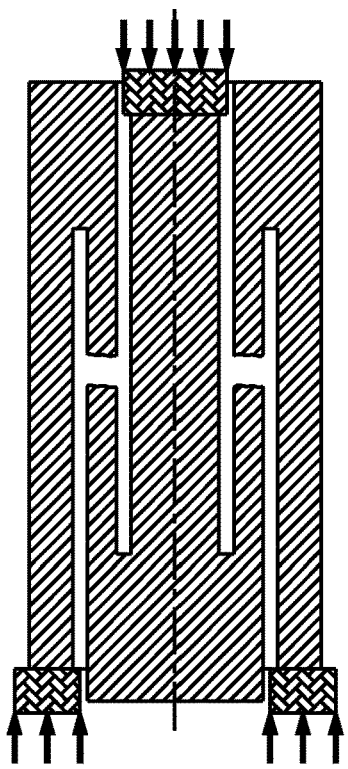
FIG. 9 is a sectional view showing a rock specimen being stretched in direct tensile test.

4) The rock mechanics testing system is operated, and pressures are loaded on the rock specimen via the cylindrical cushion block 8 and the circular cushion block 9 (as shown in FIG. 7) to stretch the rock specimen (as shown in FIG. 9), a loading rate is 0.001 mm/s, and a maximum load F=10 kN.

As shown in FIG. 7, the end face of the first cylinder 2 and the end face of the second circular body 7 are exerted with forces, and a tensile strength of the rock specimen to be tested is calculated as follows:

$$\sigma_t = \frac{F}{\pi\left(\left(\frac{d_2}{2}\right)^2 - \left(\frac{d_1 + 2b_1}{2}\right)^2\right)} = \frac{10 \times 1000 \text{N}}{\pi\left(\left(\frac{50}{2}\right)^2 - \left(\frac{25 + 2 \times 2}{2}\right)^2\right)\text{mm}^2} = 7.67 \text{ MPa}$$

Example 2

A rock specimen for direct tensile test, as shown in FIGS. 1-2, a rock body 1 of the rock specimen has the shape of a cylinder. The rock specimen of this example is the same as that of Example 1 except in the dimensions of different components. In this example, dimensions of the components are as follows:

The rock body has a diameter D of 150 mm and a height of 80 mm. A width $b_1$ of the first circular groove 3 is 5 mm, and a width $b_2$ of the second circular groove 5 is 3 mm. The first circular groove 3 has a height $h_1$ of 54 mm, and the second circular groove 5 has a height $h_2$ of 54 mm. The first cylinder 2 has the diameter $d_1$ of 50 mm, and the second cylinder 6 has a diameter $d_2$ of 75 mm. The diameter of the first cylinder 2 is an inner diameter of the first circular groove 3, and the diameter of the second cylinder 6 is an inner diameter of the second circular groove 7.

The direct tensile test of the rock specimen is conducted as follows:

1) A circular cushion block 9 is disposed on a test bench of a rock mechanics testing system, in which, an inner diameter of the circular cushion block is 78 mm, and an outer diameter of the circular cushion block is 155 mm.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 55 mm, and a center line of the cylindrical cushion block 8 coincides with the center line of the rock specimen (as shown in FIG. 7).

4) The rock mechanics testing system is operated, and pressures are loaded on the rock specimen via the cylindrical cushion block 8 and the circular cushion block 9 (as shown in FIG. 7) to stretch the rock specimen (as shown in FIG. 9), a loading rate is 0.01 mm/s, and a maximum load F=14 kN.

As shown in FIG. 7, the end face of the first cylinder 2 and the end face of the second circular body 7 are exerted with forces, and a tensile strength of the rock specimen to be tested is calculated as follows:

$$\sigma_t = \frac{F}{\pi\left(\left(\frac{d_2}{2}\right)^2 - \left(\frac{d_1 + 2b_1}{2}\right)^2\right)} = \frac{14 \times 1000 \text{N}}{\pi\left(\left(\frac{75}{2}\right)^2 - \left(\frac{50 + 2 \times 5}{2}\right)^2\right)\text{mm}^2} = 8.80 \text{ MPa}$$

Example 3

A rock specimen for direct tensile test, as shown in FIGS. 1-2, is the same as that of Example 1 except in the dimensions of different components and the shape of the rock body 1. In this example, the rock body 1 of the rock specimen has the shape of a regular square prism, and the dimensions of the components are as follows:

The rock body has a side length L of 130 mm and a height of 80 mm. A width $b_1$ of the first circular groove 3 is 10 mm, and a width $b_2$ of the second circular groove 5 is 5 mm. The first circular groove 3 has a height $h_1$ of 40 mm, and the second circular groove 5 has a height $h_2$ of 60 mm. The first cylinder 2 has the diameter $d_1$ of 38 mm, and the second cylinder 6 has a diameter $d_2$ of 75 mm. The diameter of the first cylinder 2 is an inner diameter of the first circular groove 3, and the diameter of the second cylinder 6 is an inner diameter of the second circular groove 7.

The direct tensile test of the rock specimen is conducted as follows:

1) A circular cushion block 9 is disposed on a test bench of a rock mechanics testing system, in which, an inner diameter of the circular cushion block is 80 mm, and an outer diameter of the circular cushion block is 188 mm.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 48 mm, and a center line of the cylindrical cushion block 8 coincides with the center line of the rock specimen (as shown in FIG. 7).

4) The rock mechanics testing system is operated, and pressures are loaded on the rock specimen via the cylindrical cushion block 8 and the circular cushion block 9 (as shown in FIG. 7) to stretch the rock specimen (as shown in FIG. 9), a loading rate is 1 mm/s, and a maximum load F=16 kN.

As shown in FIG. 7, the end face of the first cylinder 2 and the end face of the second circular body 7 are exerted with forces, and a tensile strength of the rock specimen to be tested is calculated as follows:

$$\sigma_t = \frac{F}{\pi\left(\left(\frac{d_2}{2}\right)^2 - \left(\frac{d_1 + 2b_1}{2}\right)^2\right)} = \frac{16 \times 1000 \text{N}}{\pi\left(\left(\frac{75}{2}\right)^2 - \left(\frac{38 + 2 \times 10}{2}\right)^2\right) \text{mm}^2} = 9.01 \text{ MPa}$$

Example 4

Figure 4:
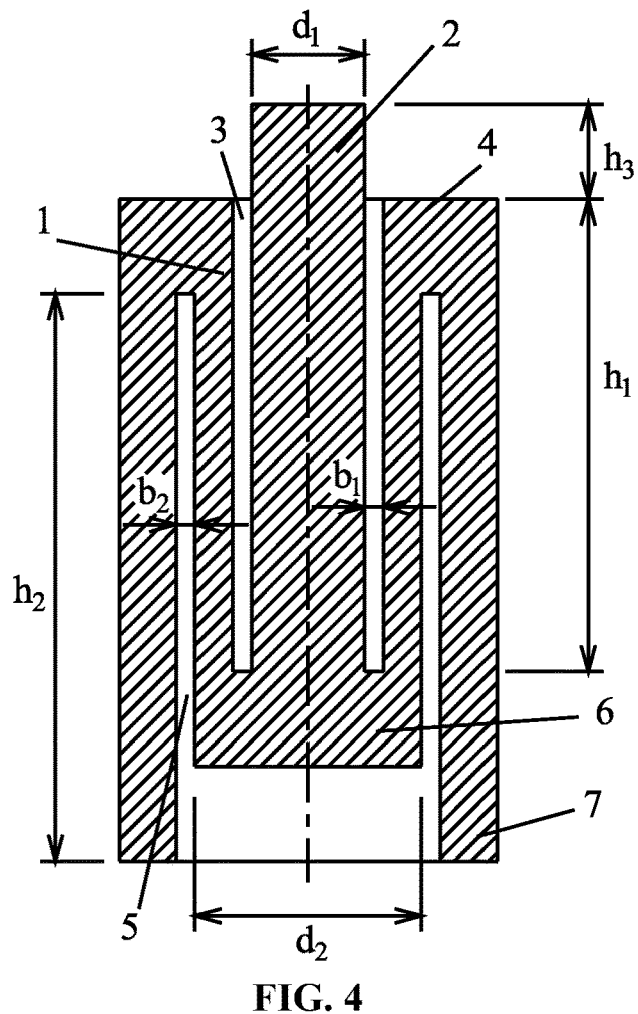
FIG. 4 is a sectional view of a second rock specimen for direct tensile testing in accordance with one embodiment of the invention.
Figure 5:
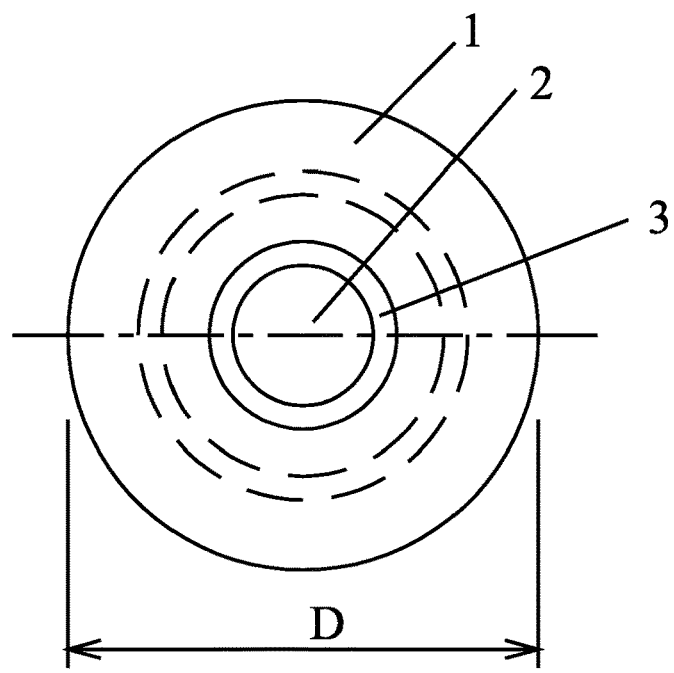
FIG. 5 is a top view of a rock body having the shape of the cylinder of FIG. 4.

A rock specimen for direct tensile test, as shown in FIGS. 4-5, a rock body 1 of the rock specimen has the shape of a cylinder. An upper end face and a lower end face of the rock body are in parallel with each other. A first circular groove 3 is disposed on the upper end face of the rock body 1 and has a circle center coinciding with a center of the upper end face of the rock body 1. A second circular groove 5 is disposed on the lower end face of the rock body 1 and has a circle center coinciding with the center of the lower end face of the rock body 1. An outer diameter of the first circular groove 3 is smaller than an inner diameter of the second circular groove 5, and the first circular groove 3 and the second circular groove 5 are staggered. The first circular groove 3 divides an upper part of the rock body 1 into a first cylinder 2 located at the center and a first circular body 4 surrounding the first cylinder 2. The second circular groove 5 divides a lower part of the rock body 1 into a second cylinder 6 located at the center and a second circular body 7 surrounding the second cylinder 6. A diameter $d_1$ of the first cylinder 2 is smaller than a diameter $d_2$ of the second cylinder 6. An end face of the first cylinder 2 is higher than the end face of the first circular body 4, and an end face of the second circular body 6 is lower than an end face of the second circular body 7. Dimensions of different components of the rock specimen are as follows:

The rock body 1 has a diameter D of 150 mm and a height of 80 mm. A width $b_1$ of the first circular groove 3 is 3 mm. A width of the second circular groove 5 is 4 mm. The first circular groove 3 has a height $h_1$ of 60 mm, and the second circular groove 5 has a height $h_2$ of 64 mm. The first cylinder 2 has the diameter $d_1$ of 50 mm, and the second cylinder 6 has a diameter $d_2$ of 75 mm. The diameter of the first cylinder 2 is an inner diameter of the first circular groove 3, and the diameter of the second cylinder 6 is an inner diameter of the second circular groove 7. A distance $h_3$ between the end face of the first cylinder 2 and the end face of the first circular body 4 is 8 mm, and a distance between the end face of the second cylinder 6 and the end face of the second circular body 7 is 8 mm.

Figure 8:
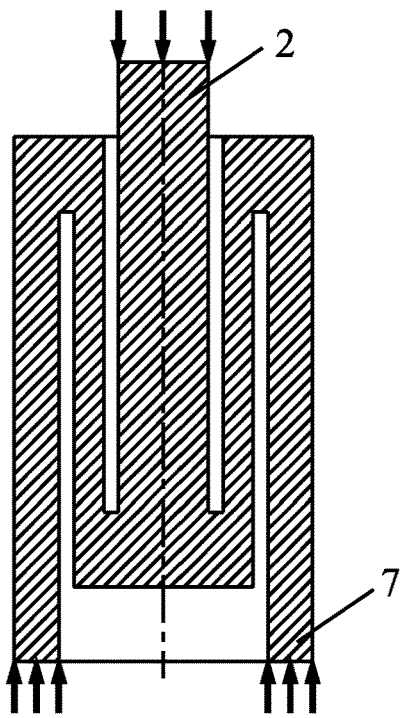
FIG. 8 is a sectional view showing a rock specimen of FIG. 4 mounted on a test bench of a rock mechanics testing system and pressures loaded on the rock specimen.

The direct tensile test of the rock specimen is conducted as follows:

1) The rock specimen is disposed on a test bench of a rock mechanics testing system to enable the end face of the second circular body 7 to contact the test bench, as shown in FIG. 8;

2) The rock mechanics testing system is operated, and pressures are loaded on the rock specimen via the end face of the first cylinder 2 and the end face of the second circular body 7 (as shown in FIG. 8) to stretch the rock specimen, a loading rate is 5 mm/s, and a maximum load F=22 kN.

As shown in FIG. 8, the end face of the first cylinder 2 and the end face of the second circular body 7 are exerted with forces, and a tensile strength of the rock specimen to be tested is calculated as follows:

$$\sigma_t = \frac{F}{\pi\left(\left(\frac{d_2}{2}\right)^2 - \left(\frac{d_1 + 2b_1}{2}\right)^2\right)} = \frac{22 \times 1000 \text{N}}{\pi\left(\left(\frac{75}{2}\right)^2 - \left(\frac{50 + 2 \times 3}{2}\right)^2\right) \text{mm}^2} = 11.25 \text{ MPa}$$

Example 5

Figure 6:
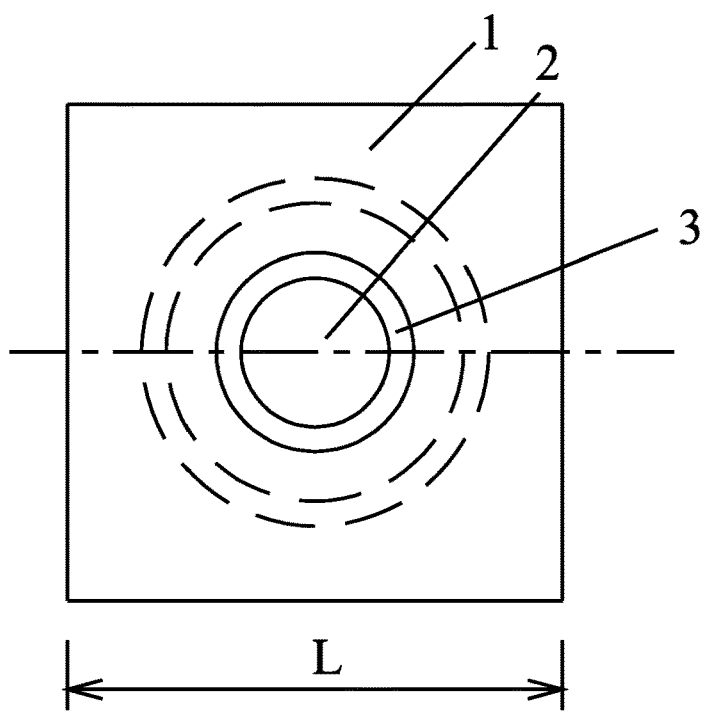
FIG. 6 is a top view of a rock body having the shape of the regular square prism of FIG. 4.

A rock specimen for direct tensile testing is shown in FIG. 4 and FIG. 6. The rock specimen of this example is the same as that of Example 1 except in the dimensions of different components. In this example, a rock body 1 of the rock specimen has the shape of a regular square prism, and dimensions of the components are as follows:

The rock body 1 has a side length L of 150 mm and a height of 90 mm. A width $b_1$ of the first circular groove 3 is 8 mm. A width of the second circular groove 5 is 10 mm. The first circular groove 3 has a height $h_1$ of 72 mm, and the second circular groove 5 has a height $h_2$ of 60 mm. The first cylinder 2 has the diameter $d_1$ of 50 mm, and the second cylinder 6 has a diameter $d_2$ of 100 mm. The diameter of the first cylinder 2 is an inner diameter of the first circular groove 3, and the diameter of the second cylinder 6 is an inner diameter of the second circular groove 7. A distance $h_3$ between the end face of the first cylinder 2 and the end face of the first circular body 4 is 5 mm, and a distance between the end face of the second cylinder 6 and the end face of the second circular body 7 is 8 mm.

The direct tensile test of the rock specimen is conducted as follows:

1) The rock specimen is disposed on a test bench of a rock mechanics testing system to enable the end face of the second circular body 7 to contact the test bench, as shown in FIG. 8;

2) The rock mechanics testing system is operated, and pressures are loaded on the rock specimen via the end face of the first cylinder 2 and the end face of the second circular body 7 (as shown in FIG. 8) to stretch the rock specimen, a loading rate is 5 mm/s, and a maximum load F=60 kN.

As shown in FIG. 8, the end face of the first cylinder 2 and the end face of the second circular body 7 are exerted with forces, and a tensile strength of the rock specimen to be tested is calculated as follows:

$$\sigma_t = \frac{F}{\pi\left(\left(\frac{d_2}{2}\right)^2 - \left(\frac{d_1+2b_1}{2}\right)^2\right)} =$$

$$\frac{60\times 1000\text{N}}{\pi\left(\left(\frac{100}{2}\right)^2 - \left(\frac{50+2\times 8}{2}\right)^2\right)\text{mm}^2} = 13.54 \text{ MPa}$$

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A rock specimen, comprising a rock body having a shape of a cylinder or a regular square prism, the rock body comprising: an upper end face, a first circular groove, a first cylinder, a first circular body, a lower end face, a second circular groove, a second cylinder, and a second circular body;

wherein
the upper end face is in parallel with the lower end face;
the first circular groove is disposed on the upper end face of the rock body and has a circle center coinciding with a center of the upper end face of the rock body;
the second circular groove is disposed on the lower end face of the rock body and has a circle center coinciding with the center of the lower end face of the rock body;
an outer diameter of the first circular groove is smaller than an inner diameter of the second circular groove, and the first circular groove and the second circular groove are staggered;
the first circular groove divides a first part of the rock body into the first cylinder located at the center and the first circular body surrounding the first cylinder;
the second circular groove divides a second part of the rock body into the second cylinder located at the center and the second circular body surrounding the second cylinder;

a diameter of the first cylinder is smaller than a diameter of the second cylinder; an end face of the first cylinder and an end face of the first circular body are disposed on a same plane; and an end face of the second cylinder and an end face of the second circular body are disposed on a same plane.

2. The rock specimen of claim 1, wherein
the diameter of the first cylinder is between ¼ and ⅓ of a diameter of the rock body having the shape of the cylinder or a side length of the rock body having the shape of the regular square prism; and
the diameter of the second cylinder is between 1.5 and 2 folds of the diameter of the first cylinder.

3. The rock specimen of claim 1, wherein a width of the first circular groove is between 2 and 10 mm; a width of the second circular groove is between 2 and 10 mm; a depth of the first circular groove is between ½ and ⅘ of a height of the rock body; and a depth of the second circular groove is between ⅔ and ⅘ of a height of the rock body.

4. The rock specimen of claim 2, wherein a width of the first circular groove is between 2 and 10 mm; a width of the second circular groove is between 2 and 10 mm; a depth of the first circular groove is between ½ and ⅘ of a height of the rock body; and a depth of the second circular groove is between ⅔ and ⅘ of a height of the rock body.

5. The rock specimen of claim 3, wherein the width of the first circular groove is between 3 and 5 mm; the width of the second circular groove is between 3 and 5 mm; the depth of the first circular groove is between ⅔ and ¾ of the height of the rock body; and the depth of the second circular groove is between ⅔ and ¾ of the height of the rock body.

6. The rock specimen of claim 4, wherein the width of the first circular groove is between 3 and 5 mm; the width of the second circular groove is between 3 and 5 mm; the depth of the first circular groove is between ⅔ and ¾ of the height of the rock body; and the depth of the second circular groove is between ⅔ and ¾ of the height of the rock body.

7. A method for testing direct tensile strength of the rock specimen of claim 1, the method comprising:
1) disposing a circular cushion block on a test bench of a rock mechanics testing system, wherein an inner diameter of the circular cushion block is smaller than an inner diameter of the second circular body and is larger than the diameter of the second cylinder, and an outer diameter of the circular cushion block is larger than a diameter of the rock body having the shape of the cylinder or a side length of the rock body having the shape of the regular square prism;
2) disposing the rock specimen on the circular cushion block, allowing a center line of the rock specimen to coincide with a center line of the circular cushion block, and allowing the end face of the second circular body to contact an end face of the circular cushion block;
3) disposing a cylindrical cushion block on the end face of the first cylinder of the rock specimen, wherein a diameter of the cylindrical cushion block is larger than the diameter of the first cylinder and smaller than an inner diameter of the first circular body, and a center line of the cylindrical cushion block coincides with the center line of the rock specimen; and
4) operating the rock mechanics testing system, loading a pressure on the rock specimen via the cylindrical cushion block and the circular cushion block to stretch the rock specimen.

8. The method of claim 7, wherein
the diameter of the first cylinder is between ¼ and ⅓ of a diameter of the rock body having the shape of the cylinder or a side length of the rock body having the shape of the regular square prism; and
the diameter of the second cylinder is between 1.5 and 2 folds of the diameter of the first cylinder.

9. The method of claim 7, wherein a width of the first circular groove is between 2 and 10 mm; a width of the second circular groove is between 2 and 10 mm; a depth of the first circular groove is between ½ and ⅘ of a height of the rock body; and a depth of the second circular groove is between ⅔ and ⅘ of a height of the rock body.

10. The method of claim 7, wherein the width of the first circular groove is between 3 and 5 mm; the width of the second circular groove is between 3 and 5 mm; the depth of the first circular groove is between ⅔ and ¾ of the height of the rock body; and the depth of the second circular groove is between ⅔ and ¾ of the height of the rock body.

* * * * *